US005582615A

United States Patent [19]
Foshee et al.

[11] Patent Number: 5,582,615
[45] Date of Patent: Dec. 10, 1996

[54] HANDLE FOR SURGICAL CLIP APPLICATOR SYSTEMS

[75] Inventors: David L. Foshee, Apex; Stephen Dawes, Raleigh, both of N.C.

[73] Assignee: Pilling Weck, Incorporated, Research Traingle Park, N.C.

[21] Appl. No.: 550,461

[22] Filed: Oct. 30, 1995

Related U.S. Application Data

[60] Provisional application No. 60/000,025 Jun. 8, 1995.
[51] Int. Cl.$^6$ .................................. A61B 17/04
[52] U.S. Cl. ..................... 606/139; 606/142; 606/143
[58] Field of Search ........................ 606/142, 143, 606/139; 227/19

[56] References Cited

U.S. PATENT DOCUMENTS

| Re. 28,932 | 8/1976 | Noiles et al. | 227/19 |
|---|---|---|---|
| 3,675,688 | 7/1972 | Bryan et al. | 227/19 |
| 4,246,903 | 1/1981 | Larkin | 606/142 |
| 4,509,519 | 4/1985 | McGarry et al. | 606/143 |
| 4,562,839 | 1/1986 | Blake, III et al. | 606/143 |
| 5,047,038 | 9/1991 | Peters et al. | 606/139 |
| 5,084,057 | 1/1992 | Green et al. | 606/142 |
| 5,104,394 | 4/1992 | Knoepfler | 606/143 |
| 5,104,395 | 4/1992 | Thornton | 606/143 |
| 5,112,343 | 5/1992 | Thornton | 606/143 |
| 5,156,608 | 10/1992 | Troidl et al. | 606/142 |
| 5,171,247 | 12/1992 | Hughett et al. | 606/142 |
| 5,403,327 | 4/1995 | Thornton et al. | 606/143 |

*Primary Examiner*—Gary Jackson
*Attorney, Agent, or Firm*—John G. Mills and Associates

[57] ABSTRACT

An improved actuator handle for a surgical instrument that can be used in endoscopic surgery with the emphasis on applying hemostatic clips. The instrument receives a longitudinal input from the actuator handle and translates the input into relative component motion to apply the hemostatic clips. The improved handle is fabricated primarily from a reusable, engineering resin having exceptional resistance to degradation by steam sterilization. Other improvements to the actuator handle include a drive stem mechanism of unitary construction that can be removed from the actuator handle as an assembled unit to facilitate sterilization. The actuator handle is provided with a quick release mechanism to facilitate the removal and replacement of the drive stem mechanism. The improved actuator handle also features a ratchet mechanism that enables the user to incrementally adjust the longitudinal input force that is transmitted to the surgical instrument and includes a switch for selective operation of the same. The actuator handle also includes a safety lock mechanism integrated into the drive stem mechanism for selective engagement of the surgical instrument and the actuator handle to prevent accidental disconnection during a surgical procedure.

7 Claims, 8 Drawing Sheets

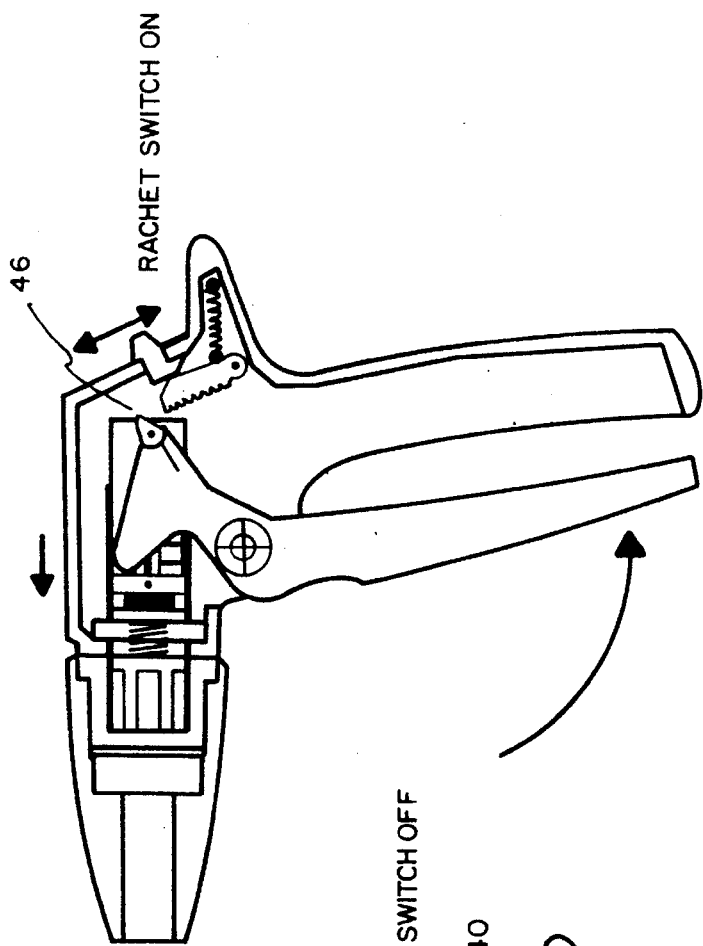
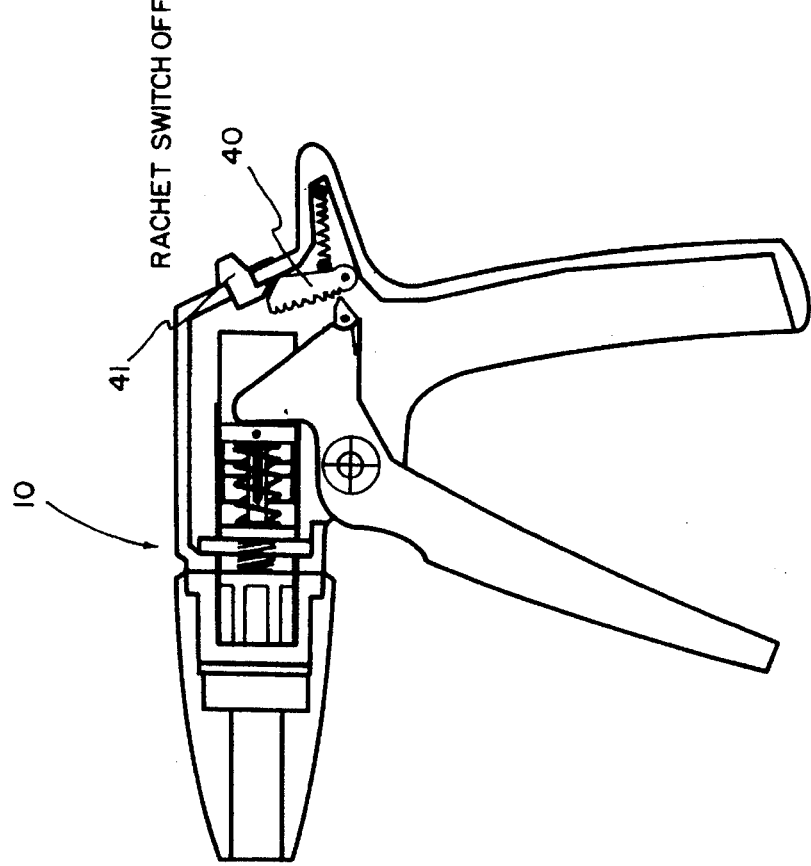

HANDLE FOR SURGICAL CLIP APPLICATOR SYSTEMS

This is a continuation of Provisional patent application Ser. No. 60/000,025, file Jun. 8, 1995, entitled Improved Handle for Surgical Clip Applicator Systems, by David L. Foshee, Stephen Dawes, Jason R. Durkin and Angela S. Phillips.

FIELD OF INVENTION

This invention relates to surgical instruments and more particularly to vessel ligation devices that can be used in endoscopic surgery for the application of hemostatic clips.

BACKGROUND OF INVENTION

The field of vessel ligation in surgery is divided into two major categories: open or traditional procedures and endoscopic procedures.

In open procedures, stainless steel, reusable instruments of traditional designs are dominant in the marketplace.

In endoscopic procedures, disposable plastic devices which automatically reload hemostatic clips predominate.

These devices need to be simplistic in construction, reliable in operation, and reasonable in cost. Instruments that come into contact with internal organs in the body must also withstand all types of sterilization. In the alternative, the construction of the instrument must be especially economical to permit disposal of the device after a single use.

In addition, the design of the instrument must provide the surgeon with a good feel during the procedure to permit as much control as possible while using the device.

In the past, various surgical instruments have been developed which satisfy some but not all of these requirements. U.S. Pat. No. 5,403,327 to Curtis W. Thornton, et al. assigned to Piling Weck, Inc., covers a surgical clip applier which features a disposable cartridge that automatically feeds fifteen clips in succession. The handle shown in this patent is of traditional style and is made of reusable stainless steel.

The advantages of the above indicated system are a lower retail price per cartridge, less storage space due to the reusable handle, and a reduced amount of medical waste which represents a reduction in disposal costs and environmental impact.

Unfortunately, many surgeons who have been trained in the use of plastic disposable endoscopic devices are uncomfortable using the heavier stainless steel handle.

Thus, the present invention represents an effort to combine the best attributes of the traditional, reusable vessel ligation instruments in a device fabricated from lightweight, sterilizable engineering resin that provides increased control and feedback in the surgeon's hand as to the procedure being conducted.

CONCISE EXPLANATION OF PRIOR ART

U.S. Pat. No. 5,403,327 to Curtis W. Thornton, et al., discloses a hemostatic clip application system having a disposal clip cartridge and a handle made of reusable stainless steel.

U.S. Pat. No. 5,047,038 to Ruldolph Peters, et al., discloses a tool for storing, dispensing and applying hemostatic clips including a shell-like housing and a pair of ring-handle actuating levers extending therefrom.

U.S. Pat. No. 5,104,395 to Curtis W. Thornton, et al., discloses an automatic hemostatic clip applicator wherein the jaws, cartridge assembly and jaw housing move together in single direction to crimp a clip resulting in a perception of little or no motion by the jaws when the applicator is activated.

U.S. Pat. No. 5,112,343 to Curtis W. Thornton discloses a hemostatic clip applier which enable the user to selectively trigger the feeding of a clip to the jaws of the applier when desired.

U.S. Pat. No. Re. 28,932 to Douglas G. Nolles discloses a surgical stapling instrument for applying sterilized staples to the disunited skin or fascia of the patent in order to effect a joining of the skill or fascia.

U.S. Pat. No. 5,104,394 to Dennis J. Knoepfler discloses an improved surgical stapler which is suitable for use in laproscopic procedures.

U.S. Pat. No. 4,562,839 to Joseph W. Blake, III, et al., discloses an instrument for applying clips to a surgical site having an applicator with two jaws which are moveable between open and closed positions.

U.S. Pat. No. 3,675,688 to Graham W. Bryan, et al., discloses a medical instrument and associated cartridge for ligating an organic tubular structure, for suturing this structure in two places with a pair of sterilized staples and for dividing the tubular structure intermediate the suturing staples.

U.S. Pat. No. 4,246,903 to Joseph F. Larkin discloses a surgical instrument having a handle and barrel. The device operates in a scissors action to compress a hemostatic clip onto a vessel.

U.S. Pat. No. 4,509,518 to Richard A. Garry, et al., discloses an apparatus for applying surgical clips to tissue including a self-contained supply of clips which may be applied through movement of the thumb and forefingers of one hand.

U.S. Pat. No. 5,084,057 to David T. Green, et al., discloses a disposable apparatus for applying surgical clips to body tissue in endoscopic surgical procedures.

U.S. Pat. No. 5,156,608 to Hans Troidl, et al., discloses a clip applicator for ligature clips particularly for laproscopic operations having a scissor-like handle.

Finally, U.S. Pat. No. 5,171,247 to J. David Hughett, et al., discloses an endoscopic clip applying system which contains a venting system and a clip applying support system which prevents closure of the mechanism before firing.

BRIEF DESCRIPTION OF INVENTION

After much research and study into the above mentioned problems, the present invention have been developed to provide a sterilizable, synthetic resin actuator handle for use in conjunction with surgical clip application system such as that shown in U.S. Pat. No. 5,403,327. The surgical clip application system disclosed therein is particularly useful for endoscopic procedures.

In the preferred embodiment of the system, a hemostatic clip applicator can be directly connected to a trigger assembly or indirectly connected to the trigger assembly through the use of an extension. The connection between the extension and the clip applicator is secured to prevent accidental release during the procedure. The applicator receives a longitudinal input and translates the input into relative component motion through the use of gearing to apply the clips.

The actuator handle of the present invention has been developed to be interchangeable with the cartridge assembly disclosed in U.S. Pat. No. 5,403,327 and to be compatible in all respects with the surgical clip application system disclosed therein.

The actuator handle of the present invention is fabricated from reusable, engineering resin and some stainless steel parts. The resin material can withstand all types of sterilization and still retain the advantages of being light in weight and as moldable as more common plastics.

An example of such a reusable, sterilizable resin is polyphenylsulfone which is sold under the trademark RADEL R-4300. This material has exceptional resistance to degradation by steam sterilization, even under stress and the presence of aggressive boiler additives.

A unique feature of the actuator handle of the present invention is a ratchet mechanism which is useful when applying hemostatic clips to vessels in the normal application of the device. The ratchet mechanism of the present invention may be turned on and off by means of a switch included within the actuator handle making the device more versatile than the prior art.

In addition, the actuator handle of the present invention includes a latch-gate system which retains the operating mechanism in the handle and provides a quick-release feature which facilitates the removal and replacement of component parts.

In view of the above, it is an object of the present invention to provide a reusable, synthetic resin actuator handle for use in conjunction with a surgical clip application system that has exceptional resistance to degradation by all types of sterilization.

Another object of the present invention is to provide an actuator handle including a ratchet means to permit selective application of hemostatic clips in a variety of surgical situations.

Another object of the present invention is to provide an actuator handle that includes a quick-release feature that enables convenient removal and replacement of the operating mechanism.

Another object of the present invention is to provide an actuator handle for use in conjunction with a surgical clip application system that provides increased control to the user during the surgical procedure.

Another object of the present invention is to provide a safety lock mechanism on the actuator handle to prevent the accidental disengagement of the same from the surgical instrument during a procedure.

Another object of the present invention is to provide an actuator handle that is of relative simple and economical construction, reliable in operation, and is of a reasonable cost.

Other objects and advantages of the present invention will become apparent and obvious from a study of the following description and the accompanying drawings which are merely illustrative of such invention.

BRIEF DESCRIPTION OF DRAWINGS

FIG. 8 is a cross-sectional view of the actuator handle showing the ratchet switch in both on and off positions;

DETAILED DESCRIPTION OF INVENTION

Figure 1:
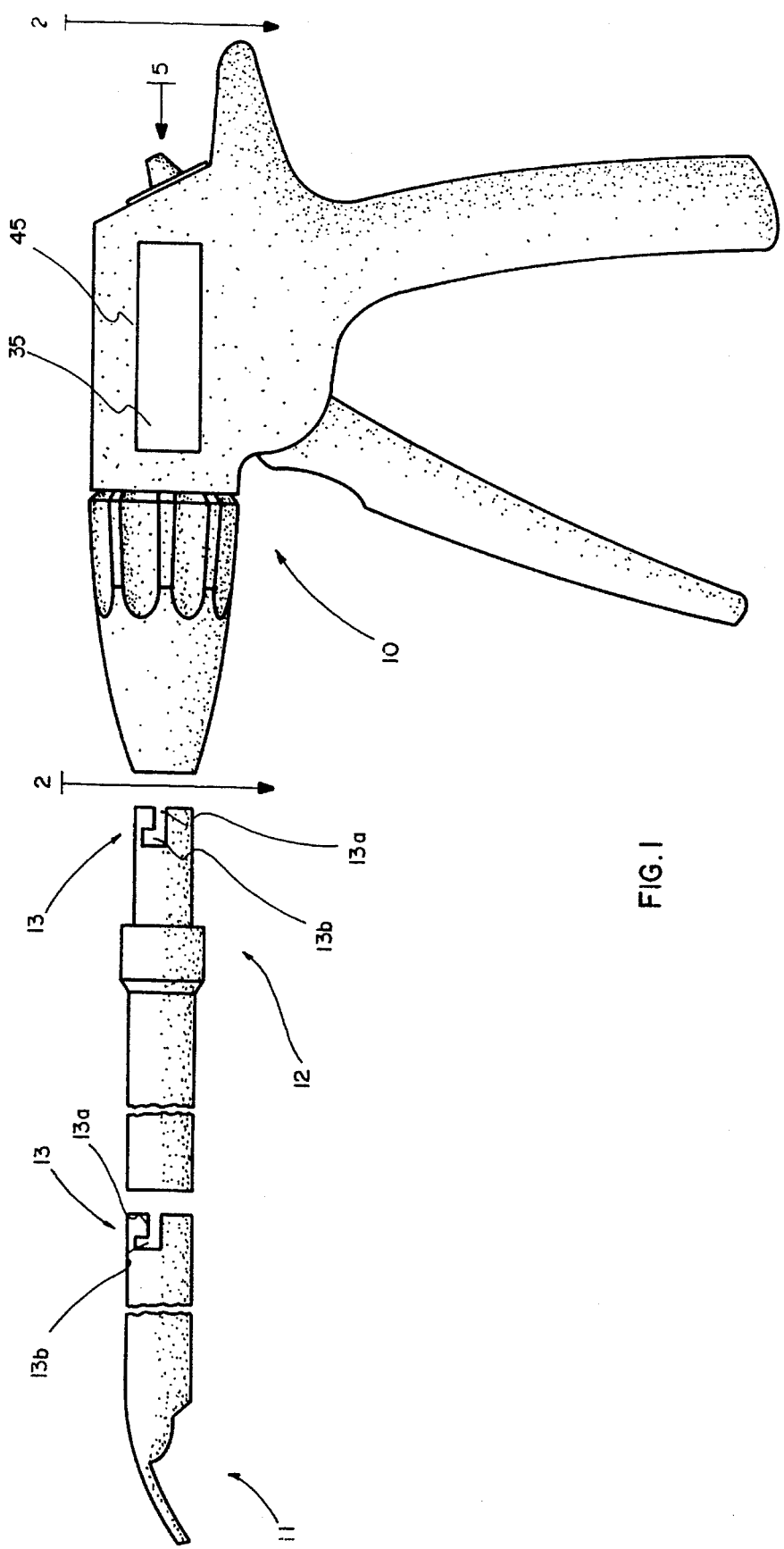
FIG. 1 is a side elevational view of the actuator handle of the present invention.

With further reference to the drawings, the improved actuator handle for use in conjunction with a surgical clip application system is illustrated in FIG. 1 and indicated generally at 10.

Before describing the actuator handle 10 of the present invention in detail, it may be beneficial to review the structure of a surgical clip application system for endoscopic or less invasive surgeries wherein the device of the present invention is to be utilized.

The major components in the hemostatic clip application system contemplated for use with the present invention are a clip applicator, indicated generally at 11; an extension member, indicated generally at 12; and an actuator handle indicated generally at 10, as shown in FIG. 1. These components can be used together or, alternatively, the actuator handle 10 can be applied directly to the clip applicator 11.

The operation of the clip applicator 11 is initiated by a longitudinal input movement supplied to clip applicator 11 by operation of actuator handle 10. Alternatively, actuator handle 10 can be used with other types of surgical instruments which are operable by longitudinal input movement which creates a relative movement in response to an input force to accomplish a surgical procedure.

Prior to getting into the details of the operation of actuator handle 10, the attachment of clip applicator 11 and extension member 12 to actuator handle 10 will be described briefly. FIG. 1 illustrates that both clip applicator 11 and extension member 12 include an L-shaped slot, indicated generally at 13, which has a longitudinal component 13a and a radial component 13b.

While only one L-shaped slot is shown for each component in FIG. 1, those skilled in the art can appreciate that a plurality of such L-shaped slots 13 can be employed for the purpose of securing the clip applicator 11 either to the extension member 12 or to the actuator handle 10 by means of a bayonet-type mounting as hereinafter described in greater detail.

The L-shaped slots 13 on the clip applicator 11 are preferably identical to the L-shaped slots on the extension member 12 for interchangeability with actuator handle 10.

Figure 2:
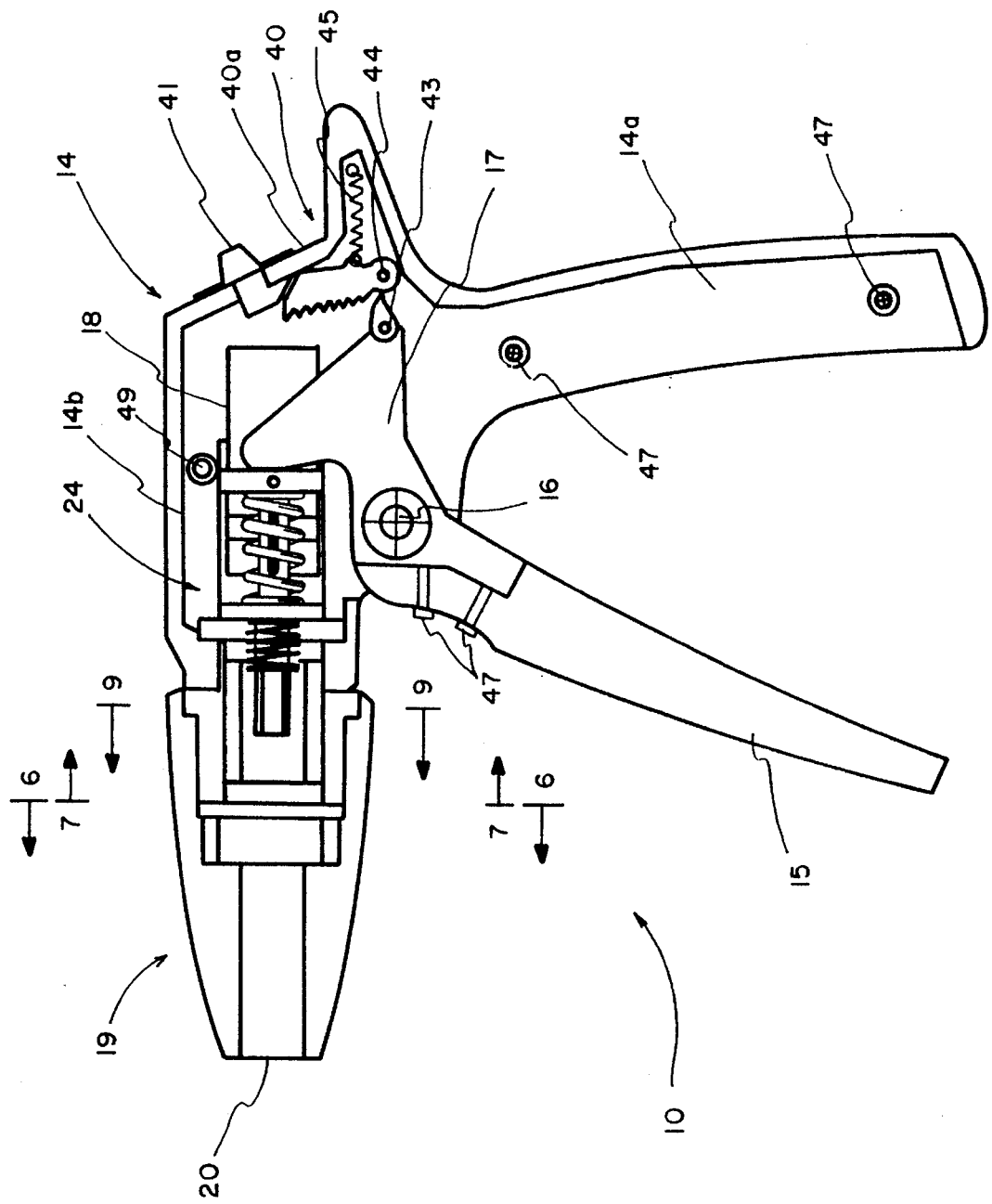
FIG. 2 is a sectional view taken through lines 2—2 of FIG. 1 showing the drive stem assembly of the actuator handle.

Referring now to FIG. 2, the details of the construction and operation of the actuator handle 10 of the present invention will be described. A generally L-shaped handle housing, indicated generally at 14, including a long leg portion 14a and a short leg portion 14b is pivotally mounted to a trigger 15 at pivot pin 16. Handle housing 14 is manufactured in symmetrical halves and assembled with a plurality of machine screws 47 or other suitable fasteners.

Trigger 15 includes a hammer 17 fixedly attached thereto and extending from a proximal end thereof. In the preferred embodiment, hammer 17 is fabricated from stainless steel and is coupled to trigger 15 by machine screws 47 or other suitable fasteners. Hammer 17 extends into a cylindrical barrel 18 formed on center axis of short leg portion 14b of handle housing 14.

In the preferred embodiment handle housing 14, trigger 15, and knob 19 are fabricated from an engineering resin such as polyphenylsulfone sold under the tradename RADEL R-4300.

Actuator handle 10 includes a generally cone-shaped knob, indicated generally at 19, including a longitudinal bore 20 extending the entire length thereof. Knob 19 is coupled to a distal end of short leg portion 14b such that bore 20 is disposed in substantial axial alignment with barrel 18.

Figure 3:
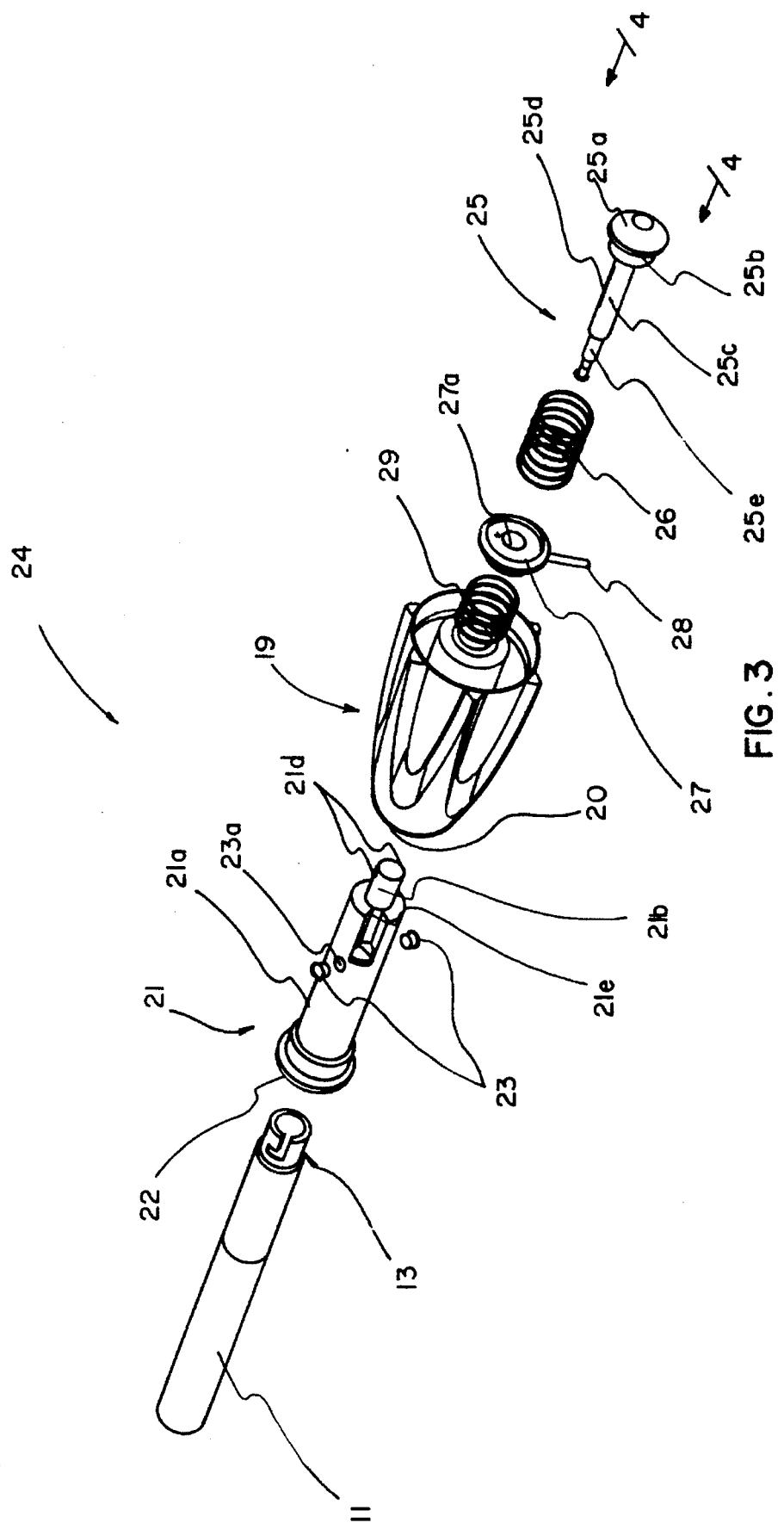
FIG. 3 is an exploded perspective view of the drive stem assembly of the present invention.

Coupling, indicated generally at 21, is installed within the longitudinal bore 20 of knob 19 as more clearly shown in FIG. 3. The outside diameter of coupling 21 is sized to a dimension that is slightly smaller than bore 20 to allow axial movement of coupling 21 in relation to knob 19.

Coupling 21 includes at least one bayonet pin 23 which extends into the internal bore 22 of coupling 21. Pin or pins 23 are mounted in a position so as to engage L-shaped slot 13 of clip applicator 11 as shown in FIG. 1. Through a bayonet-type mounting, the clip applicator 11 or extension member 12 is inserted into internal bore 22 of coupling 21 so that longitudinal component 13a of L-shaped slot 13 passes by pin or pins 23.

The clip applicator 11 is then rotated to move the radial component 13b of L-shaped slot 13 past pin or pins 23 to secure the attachment thereof. It should be noted that there is a pin 23 for each L-shaped slot 13 provided in clip applicator 11 or extension member 12.

Coupling 21 operates in conjunction with knob 19 to provide a safety lock mechanism to prevent disengagement of clip applicator 11 from actuator handle 10 as hereinafter described in further detail.

Still referring to FIG. 2 there is shown therein a drive stem assembly, indicated generally at 24, that is disposed within barrel 18 formed in handle housing 14. It will be appreciated that drive stem assembly 24 is positioned adjacent hammer 17 in functional relation thereto.

Turning now to FIG. 3 the major components in the preferred embodiment of drive stem assembly 24 are knob 19, coupling 21 including bayonet pins 23, driver, indicated generally at 25, drive spring 26, catch, indicated generally at 27, catch pin 28 and lock spring 29.

In the preferred embodiment, all of the above components of drive stem assembly 24, with the exception of knob 19, are made of corrosion resistant stainless steel to facilitate sterilization.

Driver 25 further includes a head portion 25a, a shoulder portion 25b, an elongated shaft portion 25c including an elongated slot 25d formed on the center line thereof and a drive pin portion 25e. Each of the respective features 25a, 25b, 25c, and 25e are disposed in concentric relation to the center axis of driver 25.

Catch 27 includes a catch bore 27a positioned on the center axis thereof and a catch pin hole 28a that extends radially from catch bore 27a in perpendicular relation thereto through the side wall of catch 27 to accommodate the insertion of catch pin 28 during assembly.

Still referring to FIG. 3 it will appreciated that coupling 21 is generally tubular in construction having an internal bore 22 extending therethrough. Coupling 21 includes an elongated body portion 21c having at least one bayonet pin hole 23a extending radially from internal bore 22 through body portion 21c to accommodate the insertion of bayonet pin 23 therethrough.

Coupling 21 also includes a drive pin collar 21b extending from a proximal end of coupling 21 in coaxial relation thereto wherein driver 25 is disposed after assembly is complete. It can be seen that drive pin collar 21b includes a pair of collar pin holes 21d extending radially from internal bore 22 to accommodate the insertion of catch pin 28 during assembly.

Figure 9:
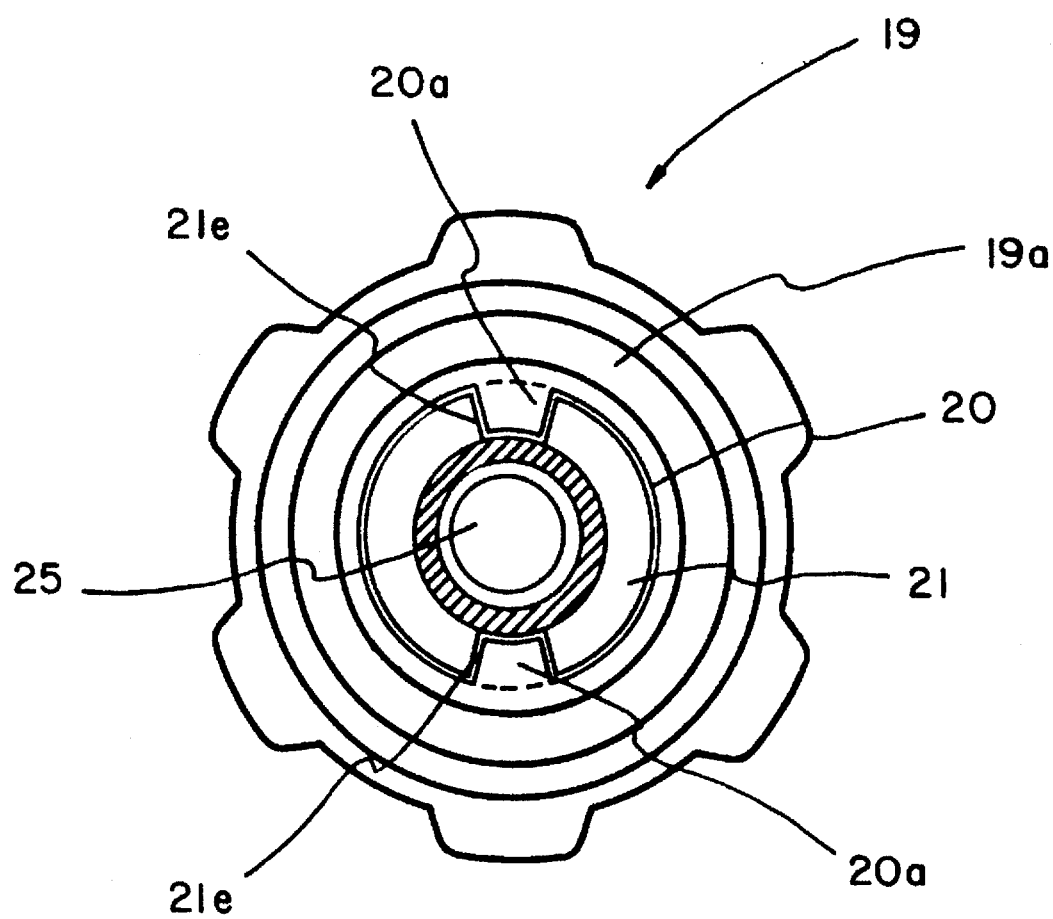
FIG. 9 is a sectional view taken through lines 9—9 shown in of FIG. 3 showing details of the safety lock mechanism.

Coupling 21 further includes at least one keyway 21e that is machined in the exterior surface of body portion 21c of coupling 21. Keyway 21e is adapted to receive a cooperating locking tab 20a formed on the interior surface of bore 20 in knob 19 as clearly shown in FIG. 9.

It will be appreciated by those skilled in the art that locking tab 20a is sized to a slightly smaller dimension than keyway 21e to permit rearward axial movement of knob 19 in relation to coupling 21.

This arrangement of locking tab 20a and keyway 21c ensures that coupling 21 and knob 19 will rotate together as a single unit and also functions as an integral feature of the safety lock mechanism.

Keyway 21e extends through a sidewall of coupling 21 at a predetermined angular relationship to bayonet pin 23 such that the locking tab 20a may engage the longitudinal component 13a of L-shaped slot 13 when clip applicator 11 or extension member 12 is inserted within coupling 21.

Thus, a safety lock mechanism is provided in the connection between actuator handle 10 and the clip applicator 11 or the extension member 12, as hereinafter described in further detail.

Figure 4:
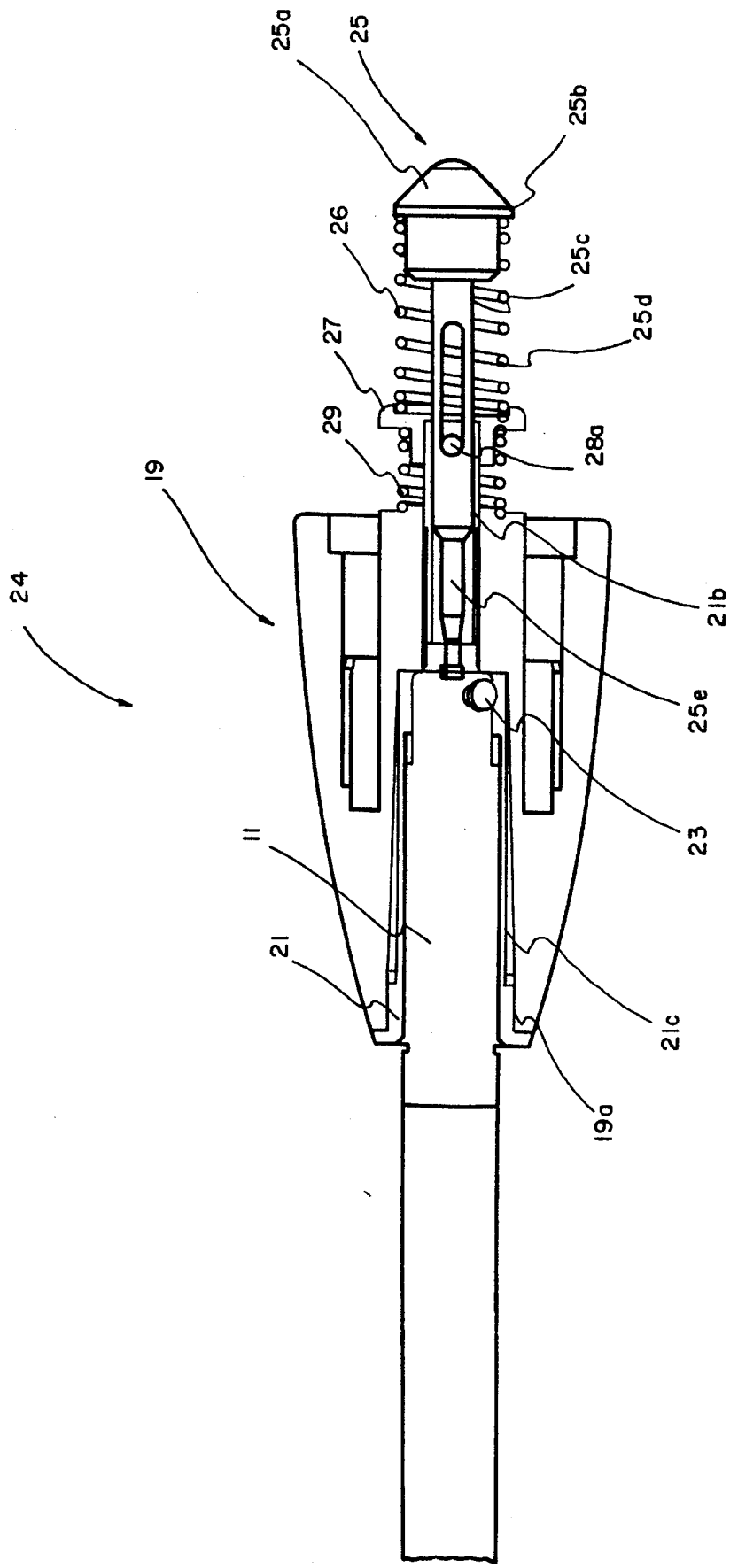
FIG. 4 is a sectional view taken through lines 4—4 of FIG. 3 showing the drive stem assembly of the present invention.

Referring now to FIG. 4 there is shown therein a detailed view of drive stem assembly 24 as an assembled unit. In an assembly procedure for the same, bayonet pins 23 are inserted into bayonet pin holes 23a so as to be flush with the exterior surface of body portion 21c. Coupling 21 may then be inserted into the internal stepped bore 19a of knob 19 which has been machined to accommodate the outside diameters of drive pin collar 21b and body portion 21c of coupling 21, with keyway 21c in alignment with tab 20a.

Driver 25 may then be inserted within drive spring 26, through catch bore 27a and thereinafter within lock spring 29 for assembly. Driver 25 is then rotated to align elongated slot 25d with catch pin holes 28a and collar pins holes 21d to permit the insertion of catch pin 28 therethrough permanently retaining the assembled components in their functional positions as shown in FIG. 4.

All of the components of stem assembly 24 having been described, the method of securing clip applicator 11 will now be described.

Clip applicator 11 is advanced proximally into coupling 21 until the longitudinal component 13a of L-shaped slot 13 registers with pin 23.

The next step requires further advancement of clip applicator 11 in the proximal direction to compress lock spring 29 which simultaneously moves knob 19 in the same direction. This movement of knob 19 slides locking tab 20a proximally within keyway 21e.

In the next step, the clip applicator 11 or extension member 12 is rotated so that the radial component 13b of L-shaped slot 13 moves past pin 23. As the rotation progresses, ultimately the longitudinal component 13a becomes aligned with locking tab 20a in knob 19. At that time, the force of spring 29 acts on knob 19 which forces tab 20a distally until it is registered in longitudinal component 13a. The force of spring 29 then retains the connection between applicator 11 or extension member 12 and actuator handle 10 preventing accidental disengagement.

It will be appreciated by those skilled in the art that coupling 21 includes a front flange 21f integrally formed therewith and extending in perpendicular relation to a center axis thereof. Flange 21f is sized to generally the same diameter as the distal end of knob 19 as clearly shown in FIG. 4.

Thus, flange 21f prevents accidental contact with the distal end of knob 19 and proximal movement of the same during use of the actuator handle 10, which might otherwise cause such disengagement.

If disconnection is desired, a force in the proximal direction must be applied to knob 19 to overcome the force of spring 29 to slide locking tab 20a proximally out of register with longitudinal component 13a of L-shaped slot 13. At that time rotation in the opposite direction of the previous rotation reverses the above steps and allows for disconnection between actuator handle 10 and clip applicator 11 or alternatively, extension member 12.

It should be noted that during a surgical procedure, the user can reorient the radial position of clip applicator 11 by applying a rotational force to knob 19. A rotational force applied to knob 19 is transmitted through coupling 21 and pins 23 which causes applicator 11 or the combination of applicator 11 and extension member 12, to rotate in response to the rotation of knob 19.

Figure 5:
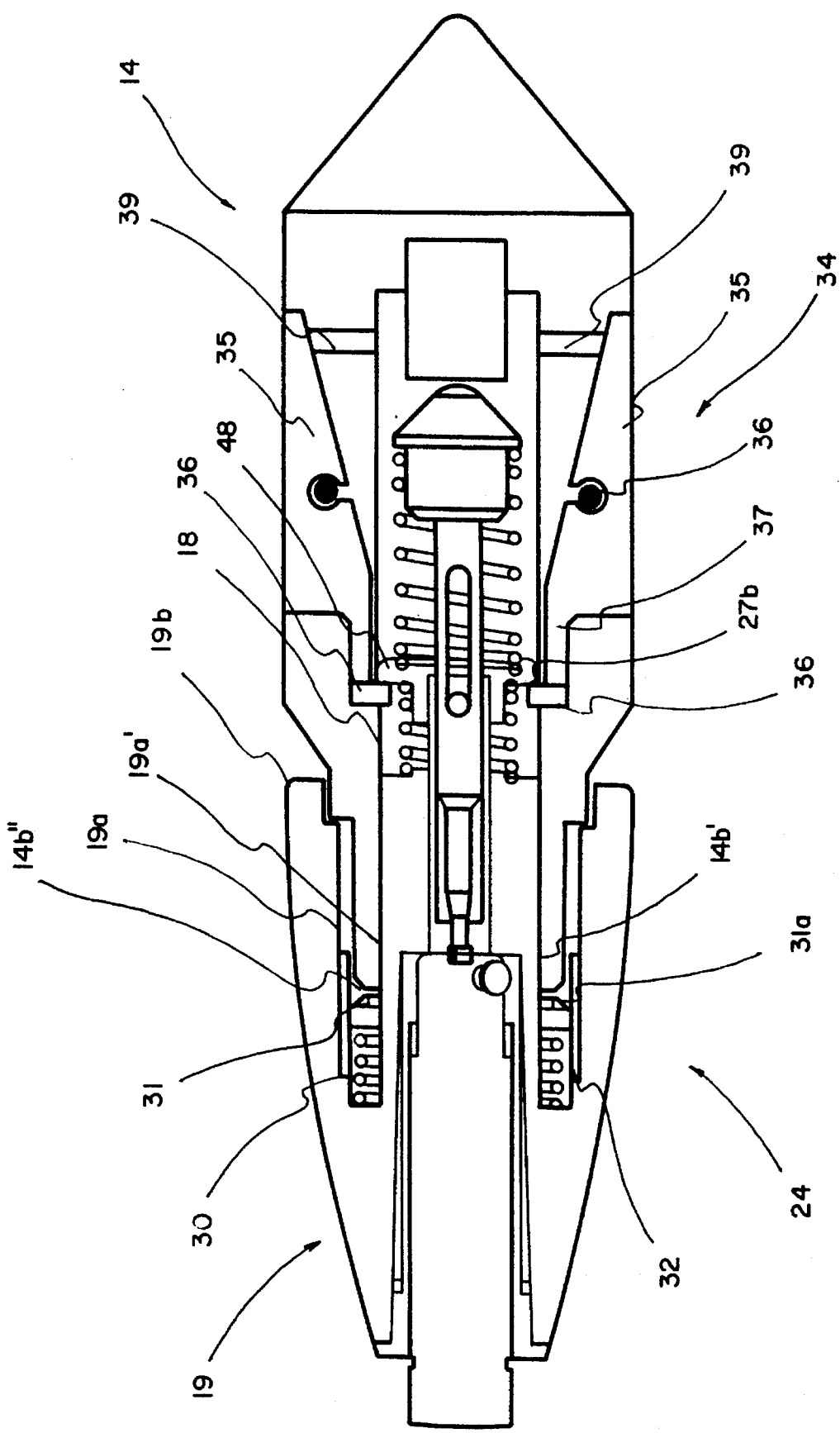
FIG. 5 is a sectional view taken through lines 5—5 of FIG. 1 showing the drive stem assembly disposed in the actuator handle.

Turning now to FIG. 5, there is shown therein a view of drive stem assembly 24 installed in handle housing 14. It can be seen that knob 19 includes a stepped groove 19a that is machined to a predetermined depth into the back face 19b of knob 19. Groove 19a is disposed about a center axis of knob 19 in coaxial relation thereto. Prior to the installation of drive stem assembly 24 into handle housing 14, detent spring 30, detent ring 31 and detent sleeve 32 are inserted into the stepped groove 19a as show in FIG. 5.

It will appreciated that a forward end 14b' of handle housing 14 is cylindrical in cross-section and machined to a dimension that is slightly smaller than an inside dimension of groove 19a. Barrel 18, defining the inside diameter of front end 14b', is sized to a dimension that is slightly larger than an inner hub 19a' of groove 19a imparting 360 degree rotation to knob 19 and drive stem assembly 24 within handle housing 14.

Figure 6:
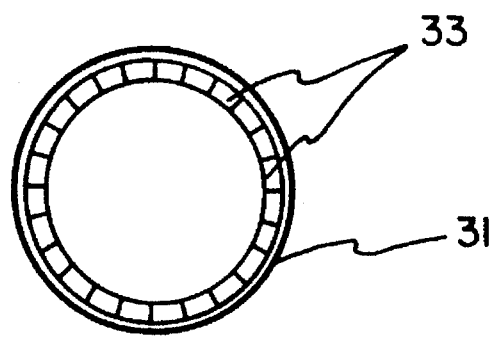
FIG. 6 is a sectional view taken through lines 6—6 of FIG. 2 showing the detent ring with serrations.
Figure 7:
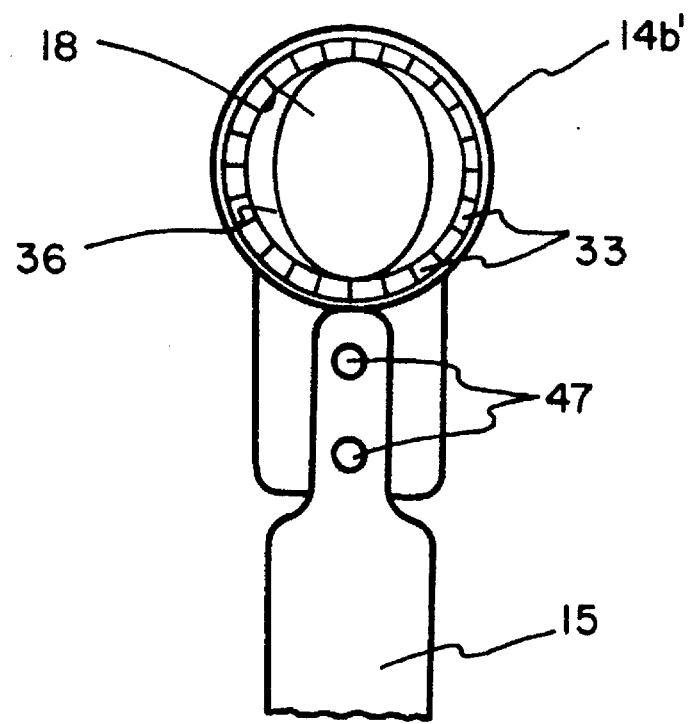
FIG. 7 is a sectional view taken through lines 7—7 of FIG. 2 showing the forward end face of the handle housing.

Referring now to FIGS. 6 and 7, FIG. 6 shows an enlarged axial view of the back end face 31a of detent ring 31 and FIG. 7 shows a detailed axial view of the front end face 14b" of forward end 14b' of handle housing 14.

It will be appreciated that both end face 31a and the end face 14b" of forward end 14b' are provided with a plurality of radially disposed serrations 33 on their opposed end faces.

Those skilled in the art will appreciate that detent spring 30 disposed in groove 19a will spring bias end face 31a of detent ring 31 against the end face 14b" of forward end 14b' thereby providing frictional resistance to the rotation of drive stem assembly 24 within handle housing 14.

This feature allows surgeons using the device to position handle housing 14 at any desired radial position relative to clip applicator 11 and to retain handle housing 14 in that position if desired.

One of the principal advantages of the present invention is that drive stem assembly 24 may be easily released from handle housing 14 for sterilization purposes.

To accomplish the quick release of drive stem assembly 24, handle housing 14 is provided with a latch-gate mechanism, indicated generally at 34, as shown in FIG. 5.

The major components in the preferred embodiment of latch-gate mechanism 34 are latch 35, gate 36, gate pin 37, pivot post 38 and latch spring 39.

Latch 35 is generally wedge-shaped in longitudinal section having a gate pin 37 projecting forwardly from its widest end.

A generally crescent-shaped gate 36 is fixedly attached to each gate pin 37 in perpendicular relation thereto such that a concave surface of the same is disposed inwardly toward a center axis of the drive stem assembly 24.

A pair of horizontally opposed latch-gate mechanisms 34 are pivotedly mounted within handle housing 14 on pivot posts 38 which are integrally formed with or fixedly attached to handle housing 14 as shown in FIG. 5. It can be seen that in this position gates 36 are disposed in parallel, spaced apart relation on either side of stem assembly 24 adjacent a forward end face 27b of catch 27.

Pivot posts 38 function as fulcrums imparting lever movement to the latch-gate mechanisms 34. Latches 35 are biased outwardly at their proximal ends by latch spring 39 such that gates 36 are urged inwardly to a positive contact with the forward end face 27b of catch 27 retaining drive stem assembly 24 in position as shown in FIG. 5.

It will be appreciated that the proximal edge of catch 27 is provided with a radius 48 to facilitate the installation of drive stem assembly 24 into latch-gate mechanism 34 as it passes through gates 36.

To release drive stem assembly 24 from handle housing 14, the user applies finger pressure to the tapered proximal ends of latches 35 which may be accessed through latch openings 45 in handle housing 14.

Thus, drive stem assembly 24 may be quickly released from handle housing 14 for removal and replacement or sterilization purposes.

Another principal advantage of the present invention can be seen by referring again to FIG. 2. Actuator handle 10 is provided with a ratchet 40 which may be selectively operated by a mechanical ratchet switch 41 at the discretion of the user.

Ratchet 40 includes an elongated body member 40a having a plurality of serrated teeth 42 disposed along one edge thereof and projecting forwardly in the direction of hammer 17.

Hammer 17 includes a pawl 43 that is fixedly attached thereto and positioned in an operative relationship with ratchet 40. In the preferred embodiment pawl 43 is pivotally mounted on hammer 17 and spring-biased in a counterclockwise direction by a pawl spring (not shown) such that pawl 43 may pivot in a clockwise motion upon engagement with teeth 42 of ratchet 40.

It can be seen that ratchet 40 is pivotedly mounted at a proximal end thereof on ratchet pin 44 imparting pivoting movement thereto.

There is also shown in FIG. 2 a ratchet spring 45 that is mechanically coupled with ratchet 40 at the back edge thereof in order to spring bias ratchet 40 in a rearward direction to a positive contact with ratchet switch 41.

Ratchet 40 is particularly useful when applying hemostatic clips (not shown) to blood vessels during surgical procedures. The ratcheting mechanism permits the user to incrementally adjust the pressure that is applied to hemostatic clips to partially crimp the same in order to position the hemostatic clip prior to its final closure about the vessel to be ligated.

In other instances when hemostatic clips are used to loosely secure catheters or to ligate large ducts, the use of ratchet 40 can prove detrimental and the user may choose to disengage ratchet switch 41.

Turning now to FIG. 8, there is shown therein a view of ratchet switch 41 in both the off and on positions. In operation of ratchet 40 the user simply depresses ratchet switch 41 downwardly when the use of ratchet 40 is desired. The downward movement of ratchet switch 41 displaces body member 40a and urges the same in a forward direction overcoming the tension of ratchet spring 45 to a position where teeth 42 may be engaged by pawl 43.

This ratcheting movement of trigger 15 permits incremental increases in pressure by the surgeon as hammer 17 acts to compress stem assembly 24 thereby advancing drive pin 25b forwardly into coupling 21. This longitudinal movement creates a relative movement within clip applicator 11 to accomplish the application of the hemostatic clips.

From the above it can be seen that the present invention provides an actuator handle that can be used in conjunction with a hemostatic clip applicator 11 and an extension member 12. The components can be used all together or, alternatively, the actuator handle 10 can be applied directly to the clip applicator 11.

Further, actuator handle 10 can be used with other types of surgical instruments which are operable by longitudinal movement which creates a relative movement in response to an input force to accomplish a surgical procedure.

The actuator handle of the present invention is fabricated from a reusable, engineering resin that has exceptional resistance to degradation by all types of sterilization providing obvious economic advantages.

Finally, the improved actuator of the present invention has a reduced number of parts and is more easily assembled than prior art devices. Yet, the present invention features a reliable ratchet mechanism and a quick-release mechanism which provide improved functional features and facilitate sterilization of the device.

The terms "upper", "lower", "side", "forward", "rearward" and so forth have been used herein merely for convenience to describe the present invention and its parts as oriented in the drawings. It is to be understood, however, that these terms are in no way limiting to the invention since such invention may obviously be disposed in different orientations when in use.

The present invention may, of course, be carried out in other specific ways than those herein set forth without departing from the spirit and essential characteristics of such invention. The present embodiments are, therefore, to be considered in all respects as illustrative and not restrictive, and all changes coming within the meaning and equivalency range of the appended claims are intended to be embraced therein.

What is claimed is:

1. An improved actuator handle for use in conjunction with a surgical instrument such as a hemostatic clip applicator which is operable by longitudinal input movement, said actuator handle including a housing which accepts an end of said instrument and a trigger assembly mechanically coupled to said housing and formed to be grasped and operated by hand, the improvement comprising:

drive stem means being of unitary construction and disposed within said housing in an operative relationship to said trigger assembly for imparting longitudinal input movement from said actuator handle to said instrument;

safety lock means on said drive stem means and on said instrument for selective engagement of said drive stem means and said instrument to prevent accidental disconnection during a surgical procedure;

quick release means disposed within said housing in a functional relationship with said drive stem means enabling removal of said drive stem means from said housing as an assembled unit; and ratchet means disposed within said housing in a functional relationship with said trigger assembly, said ratchet means being selectively operable by a switch means whereby a user of said actuator handle may incrementally adjust said longitudinal input movement transmitted to said instrument.

2. The improved actuator handle of claim 1 wherein said housing is fabricated from an engineering resin having exceptional resistance to degradation by steam sterilization.

3. The improved actuator handle of claim 2 wherein said drive stem means includes a coupling having an internal bore adapted to receive an end of said instrument within a distal end of said bore, said coupling being adapted to receive a driver means within a proximal end of said bore in an operative relationship with said instrument whereby longitudinal movement of said driver means generated by said actuator handle may be imparted to said instrument.

4. The improved actuator handle of claim 2 wherein safety lock means includes at least one bayonet pin projecting inwardly from said internal bore of said and adapted to engage; at least one L-shaped slot on said instrument; and a knob that is radially disposed about said coupling in concentric relation thereto, said knob including at least one locking tab projecting inwardly from an internal bore thereof, said tab slideably engaging a keyway formed in a sidewall of said coupling, said keyway extending through said sidewall to communicate with said internal bore of said coupling whereby said tab can register within said L-shaped slot of said instrument to selectively capture said bayonet pin within said L-shaped slot preventing accidental disconnection of said instrument and said actuator handle during a surgical procedure.

5. The actuator handle of claim 2 wherein said quick release means includes a pair of horizontally opposed latch-gate mechanisms disposed within said housing about a center axis of said drive stem means whereby said drive stem means can be conveniently removed and replaced from said housing as an assembled unit.

6. The improved actuator handle of claim 2 wherein said ratchet means includes a ratchet member that is pivotedly mounted within said housing, said ratchet member including a plurality of serrated teeth being disposed in a functional relationship with a pawl member, said pawl member being pivotedly mounted on said trigger assembly whereby said ratchet may be incrementally adjusted by the user to gradually increase the longitudinal input force transmitted to said surgical instrument.

7. The improved actuator handle of claim 6 wherein said ratchet means is selectively operated by a mechanical switch positioned within said housing in functional relation to said ratchet.

* * * * *